United States Patent [19]
Petro

[11] Patent Number: 5,259,011
[45] Date of Patent: Nov. 2, 1993

[54] METHOD AND APPARATUS FOR PATIENT HANDLING IN A COMPUTER TOMOGRAPHIC SCANNER SYSTEM

[75] Inventor: Alan Petro, Milford, N.J.

[73] Assignee: Siemens Medical Systems, Inc., Iselin, N.J.

[21] Appl. No.: 921,886

[22] Filed: Jul. 29, 1992

[51] Int. Cl.$^5$ .......................... A61B 6/04; A61G 7/08
[52] U.S. Cl. .......................... 378/4; 378/20; 378/209
[58] Field of Search ............ 378/4, 20, 204, 205, 378/208, 209

[56] References Cited

U.S. PATENT DOCUMENTS

| | | | |
|---|---|---|---|
| 4,105,923 | 8/1978 | Hynes, Jr. ........................... | 250/456 |
| 4,131,802 | 12/1978 | Braden et al. ...................... | 378/20 |
| 4,688,278 | 8/1987 | Van Aspert ........................ | 378/209 |
| 4,727,328 | 2/1988 | Carper et al. ...................... | 324/318 |
| 4,914,682 | 4/1990 | Blumenthal ........................ | 378/20 |

FOREIGN PATENT DOCUMENTS

| | | | |
|---|---|---|---|
| 0047958 | 3/1982 | European Pat. Off. ............ | 378/209 |
| 1494017 | 9/1967 | France .............................. | 378/209 |

OTHER PUBLICATIONS

Siemens "CT Trauma/ICU Stretcher", Siemens Corporation, Iselin, N.J.
Siemens "The Clinical Benefits of The Trauma/ICU Stretcher", Siemens Corporation, Iselin, N.J. no date.

*Primary Examiner*—David P. Porta

[57] ABSTRACT

A patient handling system with improved throughput is provided for a computer tomography (CT) system. A scanner room is included with the CT scanner and an associated patient bed support. Removable patient beds are attached to the tops of transportable tables initially located in first and second patient rooms located in adjacent opposite sides of the scanner room, respectively. Patients are prepared and prepositioned in the first and second patient room for later CT scanning in the scanner room. A transfer system provides for selective movement of transportable tables on tracks between the patient rooms and the patient bed support, for permitting the patient beds to be easily moved between the patient bed support and the first and second patient rooms. The beds are oriented on the transportable tables for providing alignment with the patient bed support, for facilitating transfer of the beds between the transportable tables and the patient bed support, and for quicker initiating of X-radiation scanning. The transfers can be automated through appropriate programming of a computerized control system.

20 Claims, 5 Drawing Sheets

FIG. 4
TRADITIONAL CT SCANNING

| WORK TASK | TIME REQUIRED (SECONDS) | ROOM NEEDED |
|---|---|---|
| REGISTER PATIENT | 30 | CT ROOM |
| PLACE PATIENT ON TABLE | 60 | CT ROOM |
| POSITION PATIENT | 30 | CT ROOM |
| INSERT CONTRAST INJECTOR NEEDLE IN PATIENT * | 60 | CT ROOM |
| SELECT TOPOGRAM MODE | 15 | CT ROOM |
| SCAN TOPOGRAM | 15 | CT ROOM |
| SET UP SCAN BASED ON TOPOGRAM | 30 | CT ROOM |
| CHOOSE SCAN PARAMETERS | 15 | CT ROOM |
| PERFORM CT SCAN | 60 | CT ROOM |
| CHECK INITIAL IMAGES | 25 | CT ROOM |
| ADJUST RECONSTRUCTION PARAMETERS | 10 | CT ROOM |
| SET WINDOW AND CENTER | 10 | CT ROOM |
| PREPARE CONTRAST INJECTOR * | 30 | CT ROOM |
| CHOOSE OR CONFIRM SCAN PARAMETERS | 20 | CT ROOM |
| PERFORM CT SCAN | 60 | CT ROOM |
| CHECK INITIAL IMAGES | 25 | CT ROOM |
| SET WINDOW AND CENTER | 10 | CT ROOM |
| DISCONNECT CONTRAST INJECTOR FROM PATIENT * | 30 | CT ROOM |
| REMOVE PATIENT FROM CT TABLE | 60 | CT ROOM |
| COMPLETE PATIENT EXAMINATION | 10 | CT ROOM |
| *OPTIONAL TASK | | |
| TOTAL IN CT ROOM | 605 | |

FIG. 5
CT SCANNING WITH AUTOMATED PATIENT TRANSFER SYSTEM

| WORK TASK | TIME REQUIRED (SECONDS) | ROOM NEEDED |
| --- | --- | --- |
| REGISTER PATIENT | 30 | LOAD/UNLOAD ROOM (18 OR 22) |
| PLACE PATIENT ON TRANSFER TABLE | 60 | LOAD/UNLOAD ROOM |
| POSITION PATIENT | 30 | LOAD/UNLOAD ROOM |
| INSERT CONTRAST INJECTOR NEEDLE IN PATIENT * | 60 | LOAD/UNLOAD ROOM |
| SELECT TOPOGRAM MODE | 15 | LOAD/UNLOAD ROOM |
| TRANSFER PATIENT TABLE TO CT SCAN ROOM | 60 | CT ROOM (20) |
| SCAN TOPOGRAM | 15 | CT ROOM |
| SET UP SCAN BASED ON TOPOGRAM | 30 | CT ROOM |
| CHOOSE SCAN PARAMETERS | 15 | CT ROOM |
| PERFORM CT SCAN | 60 | CT ROOM |
| CHECK INITIAL IMAGES | 25 | CT ROOM |
| ADJUST RECONSTRUCTION PARAMETERS | 10 | CT ROOM |
| SET WINDOW AND CENTER | 10 | CT ROOM |
| PREPARE CONTRAST INJECTOR * | 30 | CT ROOM |
| CHOOSE OR CONFIRM SCAN PARAMETERS | 20 | CT ROOM |
| PERFORM CT SCAN | 60 | CT ROOM |
| CHECK INITIAL IMAGES | 25 | CT ROOM |
| SET WINDOW AND CENTER | 10 | CT ROOM |
| TRANSFER PATIENT FROM CT ROOM TO LOAD/UNLOAD ROOM | 60 | CT ROOM |
| DISCONNECT CONTRAST INJECTOR FROM PATIENT * | 30 | LOAD/UNLOAD ROOM |
| REMOVE PATIENT FROM CT TABLE | 60 | LOAD/UNLOAD ROOM |
| COMPLETE PATIENT EXAMINATION | 10 | LOAD/UNLOAD ROOM |
| *OPTIONAL TASK | | |
| TOTAL IN LOAD/UNLOAD ROOM (18 OR 22) | 295 | |
| TOTAL IN CT ROOM (20) | 430 | |

METHOD AND APPARATUS FOR PATIENT HANDLING IN A COMPUTER TOMOGRAPHIC SCANNER SYSTEM

FIELD OF THE INVENTION:

The field of the present invention relates generally to patient handling methods and apparatus for X-ray scanning systems, and more particularly to computer tomographic scanner systems.

BACKGROUND OF THE INVENTION:

In any medical diagnostic system, it is important to utilize the fastest patient throughput possible, for both reducing patient discomfort, and maximizing the utilization of the diagnostic apparatus. This is particularly true in computer tomographic scanning systems. State-of-the-art computer tomography (CT) systems or scanners using electron beam deflection technology provide X-ray scanning rates that are much faster than prior CT scanners, such as those using rotating X-ray sources and detectors. The high speed CT scanners that use electron beam deflection technology removes the scanning speed of the CT apparatus as the limiting factor that reduces patient through-put. To maximize the economy of using the new high speed scanner CT apparatus, it is important to maximize the patient throughput in the associated system.

A number of prior systems have shown the use of multiple patient tables in association with scanning systems. One such system is the General Electric Signa brand MRI System, manufactured by the General Electric Corporation. The system wholly relied upon manual movement of the patient tables, and did not support patient prepositioning.

In Hynes, Jr. U.S. Pat. No. 4,105,923, entitled "PATIENT HANDLING SYSTEM AND APPARATUS FOR TOMOGRAPHIC SCANNING", a manually moveable cart incorporating a longitudinally moveable pallet section is shown. The patient is placed on the pallet on top of the cart, and moved to the CT apparatus. The patient is then wheeled manually on the cart to the CT scanning device, and the cart is positioned over an elevatable island, and secured to the island. The island is then elevated and positioned for permitting the CT scanner to scan a desired portion of the patient's body. The use of one-cart, two-cart, and three-cart systems is discussed. In the one-cart system, all preparation of the patient is performed in the CT scanner room. In the two and three-cart systems, initial preparation of the patient is performed in a room immediately adjacent to the scanner room. In the latter system, preparation and depreparation of the patient is performed in the room adjacent to the scanner room. All movement of the patient on the specially designed carts is manual, and as taught the movement cannot be direct. Also, the carts must be rotated in order to properly align them with the scanning device.

In Carper et al., U.S. Pat. No. 4,727,328, entitled "PATIENT HANDLING ARRANGEMENTS FOR NMR IMAGING SYSTEMS", a manually moveable patient cart is shown. The cart includes a patient pallet that can be locked to the top of the cart. A patient secured to the pallet is manually moved on the cart to the NMR device. The pallet is then unlocked from the cart, and moved longitudinally to position the patient as required within the cylindrical coils of the NMR apparatus. The cart has a vertically extendable platform for adjusting the height of the patient on the pallet, prior to releasing the pallet for pushing it and the patient into the NMR device.

In another known system, known as the Siemens' "Trauma/ICU Stretcher", manufactured by Siemens Corporation, Iselin, NJ, a manually moveable stretcher is supported upon the top of a wheeled cart. With the patient secured to the stretcher, the cart is wheeled adjacent to a patient bed support of a CT scanner apparatus, whereafter the stretcher can then be manually slid from the cart directly onto the patient bed support, and secured to the latter. The bed support is then operated for vertically positioning the patient, whereafter the stretcher is moveable in the horizontal plane for positioning the patient within the scanning region of the associated CT scanner. After the scanning operation is complete, the stretcher with the patient is moved back into position on the bed support. The bed support is then vertically positioned for permitting the stretcher to be slid off of the bed support back onto the cart, for moving the patient out of the scanner room.

The prior patient handling systems do not provide for direct movement or prepositioning of a patient between preparation/depreparation areas and a CT scanner room. As a result, time must be spent in positioning manually movable patient carts, for transferring a patient either to and from the patient bed supports of a scanner device, and/or for positioning the patient relative to the scanner device. Nor do the prior systems provide for automatic movement of a patient between preparation/depreparation rooms, and a CT scanner device within a scanner room.

The present inventor recognized that to reduce patient throughput time or optimize patient handling in a CT scanner system, a patient should be conveyed on a moveable cart in a straight line, with little or no rotation of either the patient or the cart being required, with the patient being prepositioned for scanning prior to entering the scanner room. Also, the present inventor recognized that by minimizing the amount of time a patient must spend within a scanner room, optimal use of the actual CT scanner apparatus for scanning the maximum number of patients possible within a given period of time will be attained.

SUMMARY OF THE INVENTION:

An object of the invention is to provide an improved method and apparatus for a patient handling system in an high speed computer tomographic scanning system.

Another object of the invention is to provide a method and apparatus for patient handling in a CT scanner system, for conveying patients in a straight line between a CT scanner device and patient loading/preparation/unloading areas.

Another object of the invention is to automate the movement of patients between CT scanner devices and patient loading/preparation/unloading areas.

Yet another object of the invention is to provide a patient handling system for a CT scanning system, in which while one patient is being moved from a CT scanner device, another patient is being moved to the device, for optimizing the use time of the device.

Yet another object of the invention is to provide a patient handling system in a CT scanner system for permitting one patient to be in preparation for entering a scanner room for CT scanning, while another patient is in the process of being scanned by the CT scanning device.

With these and other objects in mind, in the preferred embodiment, the present invention provides a patient handling system for a CT scanner apparatus that includes patient loading/preparation/depreparation/unloading staging rooms on either side of a scanner room containing the CT scanner device. Straight tracks are provided in the flooring between a patient bed support located in the scanner room, and the adjacent patient staging rooms, respectively. A first patient is loaded onto a bed in one of the loading rooms, and prepared to the maximum extent possible for scanning by the CT scanner, including being prepositioned for scanning. At the same time, a second patient may be in the process of being scanned by the CT scanner device. When scanning of the second patient is completed, that patient is removed from the patient bed support by sliding a patient pallet or bed from the support directly onto a patient cart or table, whereafter the cart is moved along a straight track from the scanner room into the other patient staging room. At the same time, the system operates for initiating movement of the first patient from the one patient loading/unloading room along another straight track, to position the patient adjacent to the patient bed support in the scanner room, whereafter the patient bed or stretcher is slid onto the patient bed support. Preparations are then completed for scanning the new patient, and the scanning process is initiated. During this time, the previously scanned second patient is deprepared in the other patient room, and unloaded from the patient bed after depreparation is completed. A third patient may then be loaded onto the now empty patient bed in the second patient room. When scanning of the second patient is completed, that patient's bed or stretcher is slid from the patient bed support back onto the patient cart, and the cart moved along the track for moving the patient back into the associated one patient room. If preparation of the third patient has been completed, that patient can be moved into the scanner room at the same time that the other patient is being moved back to the first patient room. Although the patient beds or stretchers can in one embodiment be manually moved along the tracks between the patient rooms and the scanner room, in the preferred embodiment all patient movement is automated through the use of motorized movement systems. In such automated systems, the track can actually be a motorized conveyer for moving the patients on their beds or tables, or the beds or tables can be provided with known mechanisms for in combination with the track moving the bed along the track. An appropriately programmed control system can be included for completely automating all movement of the patients, in conjunction with operation of the CT scanner device. In a preferred embodiment for a two-bed patient handling system, patient movement is bidirectional, that is a patient is moved between one patient room and the scanner room, and then back to the original patient room in which they were prepared. The patient is then deprepared and unloaded, while another patient is being finally prepared and scanned.

BRIEF DESCRIPTION OF THE DRAWINGS:

The present invention will be described in detail below with reference to the drawings, in which like items are identified by the same reference designation, wherein:

FIG. 4 shows a time and motion study analysis for the various work tasks performed in a typical CT scanning system.

FIG. 5 shows a time and motion study analysis for a CT scanning system incorporating one embodiment of the present invention.

Figure 1:
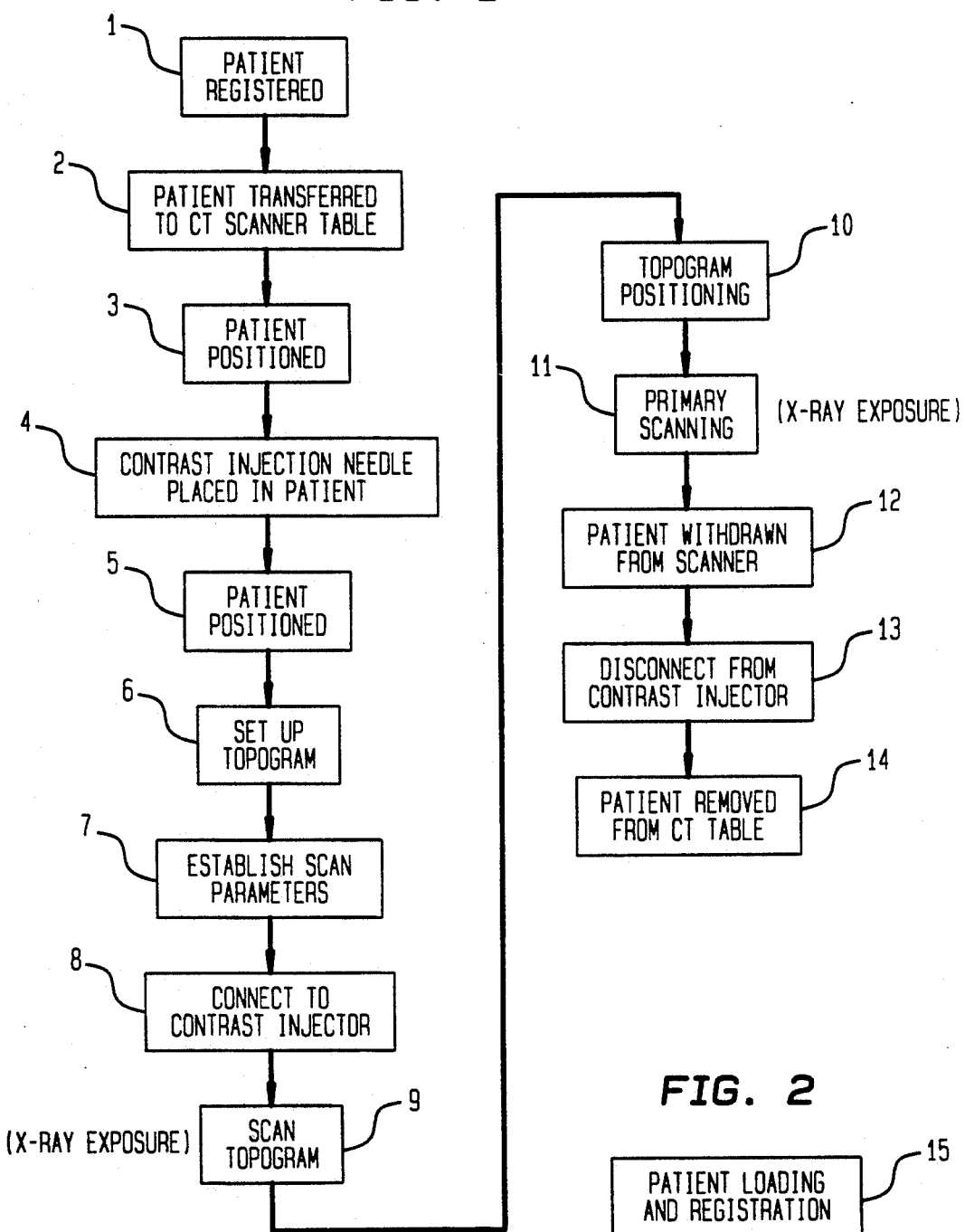
FIG. 1 is a flowchart showing sequential steps performed in a typical CT scanner system for scanning a patient.

DETAILED DESCRIPTION OF THE INVENTION:

With reference to FIG. 1, a typical CT scanning system includes steps 1 through 14, as shown. All of these steps are known by those of ordinary skill in the art, and will not be described in detail here. Note that previously cited Hynes, Jr. U.S. Pat. No. 4,105,923 describes a number of these steps in detail, and discusses problems associated therewith. In FIG. 1, it is shown that in the typical CT scanning system, once a patient is registered, all steps through the scanning of the patient are carried out in the scanning room, with the patient on the CT scanner table. This means that all of the preparation of the patient prior to scanning must be made in the scanner room where the CT scanner device is located. The present inventor recognized that if a patient is prepared in other than the scanning room for at least a major portion of the preparation steps required prior to scanning, and then moved into the scanner room, patient throughput could be improved. He also recognized that if a patient is prepared in a separate area or room on a bed, prepositioned for scanning on the bed, and after preparation preferably automatically moved on the bed in a straight line over the shortest distance possible for positioning of the bed on a bed support of the CT scanner system, and thereafter moved on the same bed from the bed support in a straight line back to a depreparation/unloading room, that patient throughput is substantially improved.

Figure 2:
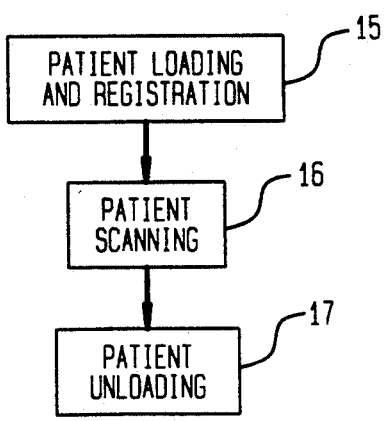
FIG. 2 is a simplified flowchart for one embodiment of the invention showing three areas between which a patient must be shifted in undergoing a CT scan procedure.

A simplified flowchart for an embodiment of the invention using at least two patient beds, and preferably an automated transfer system for shifting patients on their beds between various areas, is shown in FIG. 2. These three areas 15, 16, 17 can each represent individual adjacent rooms or screened off areas. As shown, in a first area 15 a patient is registered, loaded upon a CT scanner bed, and prepared for the scanning process to the greatest extent possible. After preparations are completed for scanning, the patient is moved to a second area 16 for scanning by the CT scanner device. Once scanning is completed, the patient is then moved to an area 17 away from the CT scanner device area for depreparation, and unloading. The latter area 17 can be the original area 15 where the patient started or a unique third area 17. These three operational areas are designated as functional areas 15 through 17 in FIG. 2.

Figure 3:
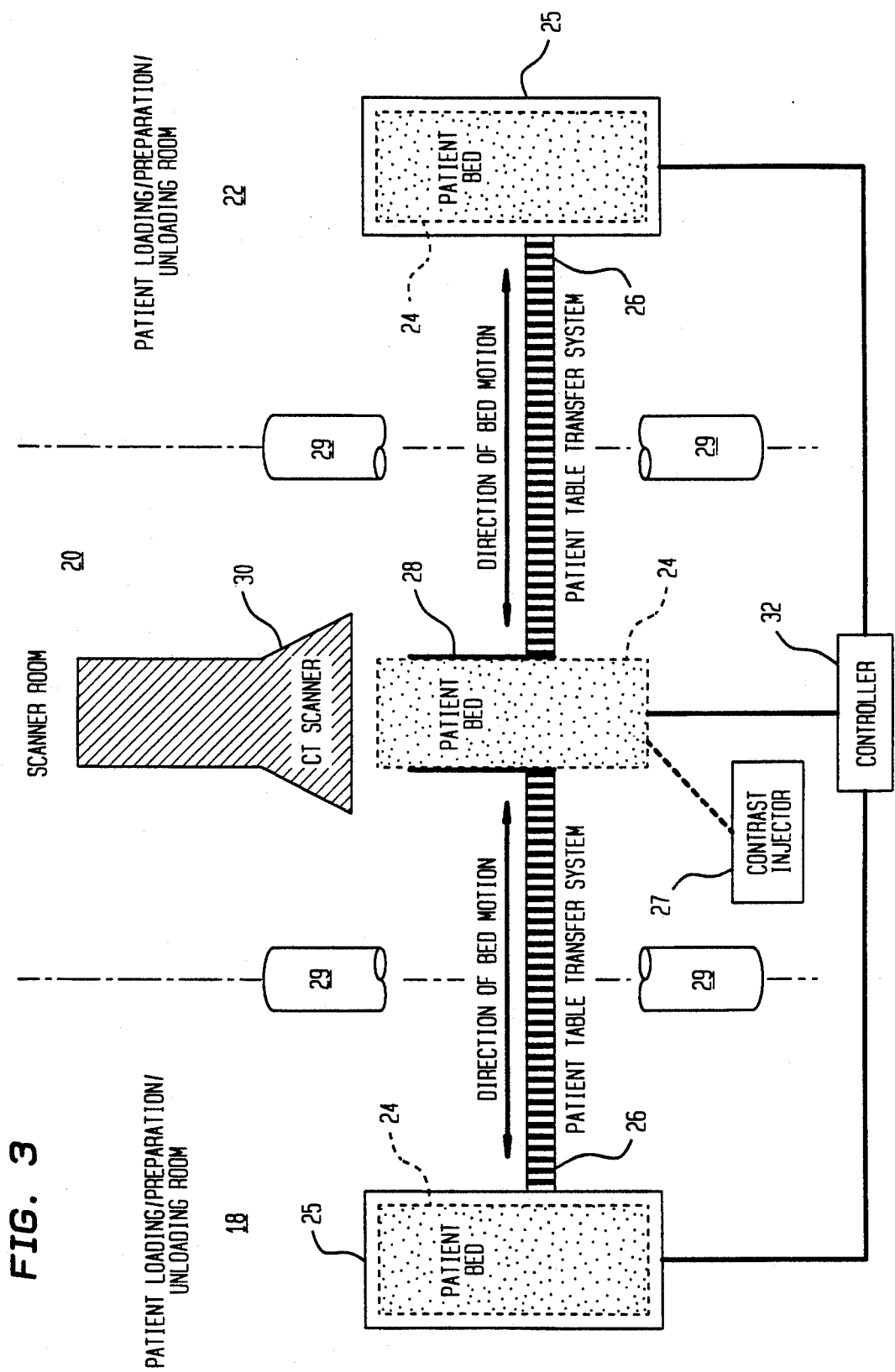
FIG. 3 shows the layout of adjacent rooms in one embodiment of the invention for patient handling in a CT scanner system.

In FIG. 3, a simplified diagram is shown for a preferred embodiment of the invention including three adjacent rooms 18, 20, and 22, showing required elements in each room. As shown, the first and second rooms, 18, 22, respectively, are each provided for patient loading/preparation/unloading. If desired, each room can also be used for patient registration in addition to other of the functions. The scanner room 20 is located between the first and second rooms 18 and 22, respectively. Note that instead of providing individual rooms 18, 20, and 22, the present invention can be provided in one large room, with the areas 18, 20, and 22 separated by appropriate privacy screens, movable doors, or curtains 29, designed to shield from scattered X-radiation. Accordingly, in this description of the invention, the use of the wording room or area are meant to be interchangeable.

With further reference to FIG. 3, the first room 18 includes a patient bed 24, that is mounted on a patient table or cart 25, in turn mounted on a track or conveyor system 26 for moving the bed 24 preferably in a straight line, from the first room 18 onto a patient bed support 28 for a CT scanner apparatus 30 located in the adjacent scanner room 20. The second patient loading/preparation/unloading room 22 on the other side of the scanner room 20 also includes a patient bed 24, and a track or conveyor type transfer system 26, for moving the bed 24 from that room onto the patient bed support 28 in the scanner room 20. Additional description for track or conveyor system 26 is given below.

In a preferred completely automated embodiment of the present invention, controller 32 is provided by a suitably programmed computer or microprocessor, for example, for controlling the movement of the beds 24 upon carts or patient tables 25, between scanner or CT room 20 and an associated one of the adjacent patient rooms 18 and 22, respectively. In one embodiment of the invention, the patient beds 24 are provided by a Siemens' CT Trauma/ICU Stretcher, manufactured by the Siemens Corporation, Iselin, New Jersey. As previously described, such stretcher units include a removable stretcher attached to a special cart mechanism. For use in the present invention, the cart mechanism can be easily modified to be mounted upon the patient tables 25 of the associated conveyor or track-based transfer system for moving the patient between rooms, as indicated. Other mobile patient bed systems may also be used, and modified as required to travel along the conveyor of track 26.

In a two patient bed 24 embodiment of the invention, with further reference to FIG. 3, operation of the patient handling system will now be described. A first patient enters the system in room 18, for example, where the patient is first registered. Thereafter, the patient is placed on the associated patient bed 24, and prepared for the scanning operation to the greatest extent possible. It is first necessary to position the patient on the patient bed 24 for required scanning, whereafter a contrast injector needle (not shown) is inserted into the patient. Also, a topogram mode is selected by the technician.

Next, the patient bed 24 is automatically moved from room 18 on the patient table transfer system or track 26, preferably in a straight line, as shown, into scanner room 20 to a position immediately adjacent to the patient bed support 28. The patient bed 24, that is the associated stretcher carrying the patient on the top of a movable cart or table 25 is transferred from the cart 25 onto the patient bed support 28, in this example. The scan topogram is then performed, followed by setting up the scan based upon data obtained from the scan topogram. The CT scanner 30 is operated to perform the CT scan of the patient who has been previously appropriately positioned within the CT scanner 30 via the movement of the bed support 28. Initial images are checked by the technician or radiologist, followed by adjustment of reconstruction parameters. The contrast injector 27 is prepared and attached to the patient with previously inserted needle. Scan parameters are then chosen and confirmed, whereafter a CT scan is performed. Initial images are checked. The window is set and centered. The X-ray exposure to the patient has now been completed. The patient bed or stretcher 24 in this example, is then moved from the patient bed support 28 back onto the movable cart or table 25. Patient bed 24 is then automatically moved back into room 18 for patient depreparation, and unloading.

At the time of initiating transfer of this first patient back into room 18, another patient previously registered and loaded onto a patient bed 24 in room 22, ideally would undergo preparation while the first patient is being scanned with X-radiation, and can now be automatically moved upon their patient bed 24 into the scanner room 20. The movement of the patient beds 24 can be coordinated so that as one patient bed 24 is leaving scanner room 20, the other patient bed 24 is entering the scanner room 20. Obviously, the first patient to enter the system can do so in either one of rooms 18 or 22. Once operation of the system has been initiated in this embodiment, two patients can be processed in the system at any given time.

As illustrated in this example, typically when one patient is being scanned, another is being prepared, and as one patient is entering the scanner room 20, another patient is leaving the scanner room 20 for depreparation and unloading. Note as illustrated for this embodiment, patient beds are moved bidirectionally in a straight line between their associated Room 18 and 22, and the scanner room 20. A patient bed 24 always is returned from the scanner room 20 back to one of the rooms 18 or 22 where the patient bed 24 was initially located.

As illustrated, the preferred embodiment of the invention includes an automated transfer system for transferring patient beds 24 between patient rooms 18 and/or 22 and scanner room 20. However, where cost is a primary concern, the automated transfer system can be replaced with a manual transfer system. In such an alternative embodiment, the patient table transfer system would still include a track 26 upon which the patient beds 24 are mounted. However, the beds 24 must be manually pushed along the tracks 26 between Rooms 18 and 20, and Rooms 22 and 20. Also, the patient beds 24 must be manually moved from their associated carts 25 onto the patient bed support 28, and therefrom back onto the associated cart 25.

The present inventor performed a CT Time and Motion Analysis for a traditional CT scanning system, and also for a CT scanning system with a preferred automated transfer system of the present invention. As a result of this analysis, he found that it is possible to reduce patient time in the CT scanner room 20 by more than 28% using the present invention. Reference is made to FIG. 4 for showing the CT time and motion analysis for the traditional CT scanning system. Also, reference is made to FIG. 5 showing a table for the CT time and motion analysis for a CT scanning system incorporating the present automated patient transfer system.

As described above, the present invention provides a transfer system that is automated, avoids collisions between patient carts 25, and ensures X-radiation is not initiated while support personnel are in scanner room 20. The automation can be extended to include auto securing mechanisms for preventing movement of cart 25 and/or bed 24 at times that contrast injector 27 is connected to a patient.

Figure 6:
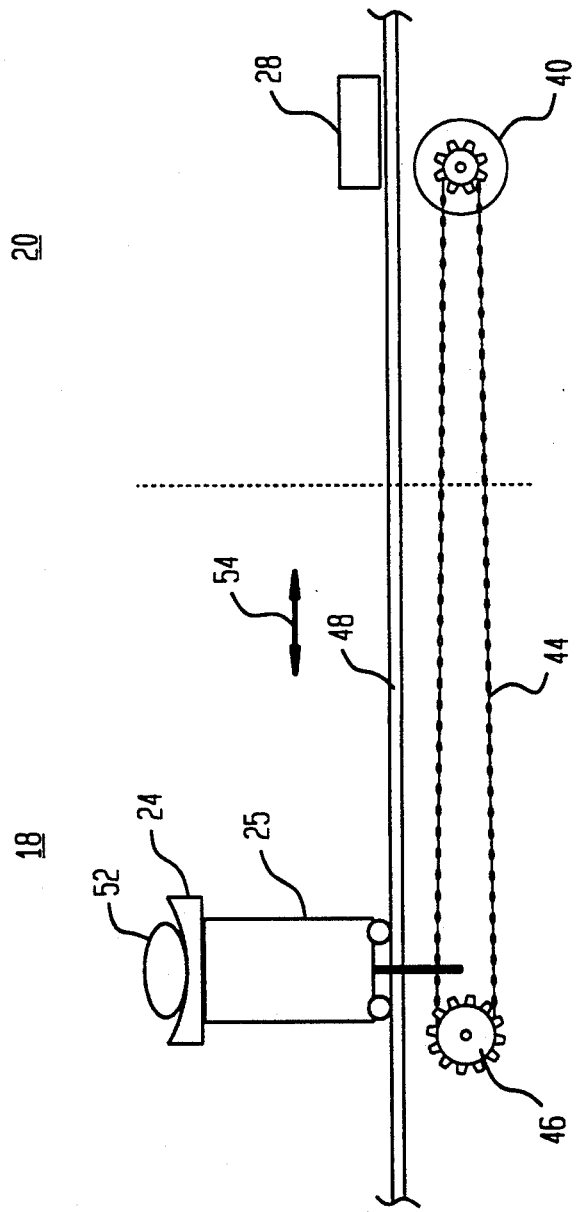
FIG. 6 shows a simplified cutaway view of a transfer system for one embodiment of the invention.

Although the preferred embodiments of the invention have been shown and illustrated herein, various modifications to these embodiments may occur to those of skill in the art. Any such modifications are meant to be covered by the spirit and scope of the appended claims. For example, as shown in FIG. 6, the transfer system 26 is provided by a motor 40 operable for selectively rotating a drive gear 42 in a clockwise or counterclockwise direction. Drive gear 42 is connected to a chain or toothed belt or similar motive transfer element 44 at one end. The other end of chain 44, in this example, is connected around a toothed idler gear 46. The transfer system 26 is mounted beneath the flooring between rooms 18 and 20, in alignment with a narrow open slot 48 in the floor. A rod or connecting arm 50 is rigidly connected at one end to the top of chain 44, and at its other end through slot 48 to the lower portion of patient table or cart 25. A removable bed 24 carrying a patient 52 is mounted on top of cart 25. Motor 40 is operated for clockwise rotation of chain 44 to move cart 25 from room 18 to room 20 to a position adjacent patient bed support 28, in this example. Motor 40 is operated for counterclockwise rotation of chain 44 for moving cart 25 back to room 18. Other track or conveyor systems 26 can be provided, such as hydraulic transfer systems, or motorized rack and pinion systems, for example. These and yet other systems for providing transfer system 26 are believed well known to those of ordinary skill in the art of factory automation. Specific design choices will depend upon the particular application, and the user's design criteria.

What is claimed is:

1. A patient handling system for a computer tomography (CT) system, comprising:
    a scanner room;
    a CT scanner located in said scanner room;
    a patient bed support located in said scanner room for positioning a patient on a patient bed for scanning by said CT scanner;
    a first patient staging room located adjacent to one side of said scanner room for preparing a patient for scanning;
    a first transportable table located in said first patient staging room;
    a first patient bed removably attached to the top of said first transportable table; and
    transfer means for selectively directing the movement of said first transportable table carrying a prepositioned patient on said first patient bed directly from said first patient staging room along a predetermined path to a position in said scanner room immediately juxtaposed to one side of said patient bed support, for permitting without jockeying of said first transportable table, transfer of said first patient bed on to said patient bed support, for permitting a CT scanning procedure to be conducted on said patient, whereafter said patient on said first patient bed is transferred back onto transportable table, for return along said predetermined path of said transfer means to substantially the identical starting position in said first patient staging room;
    wherein said transfer means includes means for automating the movement and transfer of said first patient bed to and from said scanner and first patient staging rooms, and to and from said patient bed support and first transportable table.

2. The CT patient handling system of claim 1, wherein said transfer means includes a first track upon which said first transportable table travels between the patient bed support in said scanner room, and said first patient staging room.

3. The CT patient handling system of claim 2, wherein said first track is straight for carrying said first patient bed on said first transportable table along a straight line bidirectionally between said first patient staging room and said scanner room.

4. The CT patient handling system of claim 1, further including:
    second patient staging room located adjacent to the other side of said scanner room for preparing a patient for scanning;
    a second transportable table located in said second patient staging room; and
    a second patient bed removably attached to the top of said second transportable table;
    said transfer means also including means for selectively directing the movement of said second transportable table carrying a prepositioned patient on said second patient bed directly from said second patient staging room along a predetermined path to a position in said scanner room immediately juxtapositioned to the other side of said patient bed support, for permitting without jockeying of said second transportable table, transfer of said second patient bed onto said patient bed support, for permitting a CT scanning procedure to be conducted on the associated patient, whereafter the patient on said second patient bed is transferred back onto said second transportable table, for return along the associated predetermined path to substantially the same starting position in said second patient staging room.

5. The CT patient handling system of claim 4, wherein said transfer means includes first and second tracks respectively between the patient bed support in said scanner room, and said first and second patient staging rooms, respectively, upon which tracks said first and second transportable tables travel, respectively.

6. The CT patient handling system of claim 5, wherein said first and second tracks are straight for moving said first and second patient beds on said first and second transportable tables, respectively, along a straight line bidirectionally between said scanner room and said first and second patient staging rooms, respectively.

7. The CT patient handling system of claim 5, wherein said transfer means includes movement and transfer of said first and 3 second patient beds, respectively, to and from said scanner room and each of said first and second patient staging rooms, respectively, thereby permitting one patient bed to enter the scanner room as another patient bed is leaving the scanner room.

8. The CT patient handling system of claim 4, wherein said transfer means includes movement and transfer of said first and second patient beds, respectively, to and from said scanner room and each of said first and second patient staging rooms, respectively, thereby permitting one patient bed to enter the scanner room as another patient bed is leaving the scanner room.

9. In a CT patient handling system for a computer tomography (CT) scanner, a method comprising the steps of:
   locating said CT scanner and its associated patient bed support in a scanner room;
   providing first and second patient preparation/depreparation rooms adjacent to and on opposite sides of said scanner room;
   installing first and second patient table transfer systems between said scanner room, and said first and second patient rooms, respectively, for moving patients on beds directly from their associated rooms onto said patient bed support for scanning by said CT scanner, and for returning said patients on their beds directly back to their associated rooms;
   positioning first and second patient beds on said patient table transfer systems, respectively, for pre-orientation with said patient bed support to facilitate transfer of said first and second patient beds between said first and second patient table transfer systems, respectively, and said patient bed support; and
   automating the operation of said first and second patient table transfer systems, for automatically transferring patients on their beds between said first and second patient rooms, respectively, and said patient bed support in said scanner room.

10. The method of claim 9, further including the steps of:
    preparing one patient on a patient bed in one of said first and second patient rooms for scanning, while another patient previously prepared in the other of said first and second patient rooms is being scanned by said CT scanner; and
    coordinating the operation of said first and second transfer systems for initiating the movement of said one patient into said scanner room, as said another patient is being moved out of said scanner room.

11. The method of claim 9, further including the steps of:
    installing a first track between one side of said patient bed support in said scanner room and a predetermined position in said first patient room, for permitting said first patient table transfer system to bidirectionally move upon said first track directly therebetween; and
    installing a second track between another side opposite said one side of said patient bed support and a predetermined position in said second patient room, for permitting said second patient table transfer system to bidirectionally move upon said second track directly therebetween.

12. The method of claim 9, further including the steps of:
    preparing first and second patients in said first and second patient rooms, respectively, for scanning; and
    depreparing said first and second patients in said first and second patient rooms, respectively, after CT scanning;
    said preparing and depreparing steps being made to minimize the actual time said first and second patients must spend in said scanner room.

13. The method of claim 12, wherein said preparing step for each of said first and second patients, further includes the steps of:

registering said patient;
placing said patient on an associated bed transfer table attached to the top of the associated one of said first and second patient table transfer systems;
positioning said patient for scanning;
inserting a contrast injector needle, as required, in said patient; and selecting a tomogram mode.

14. The method of claim 13, wherein said depreparing step for each one of said first and second patients, further includes the steps of:
    disconnecting the contrast injector, as required, from said patient;
    removing said patient from the associated said first or second transfer table; and
    completing the examination of said patient.

15. In a computer tomography (CT) system, a method for patient handling comprising the steps of:
    installing a CT scanner and its associated patient bed support in a scanner room;
    installing a first track between one side of said patient bed support and a point in a first patient room;
    removably attaching a first patient bed to the top of a first transportable table mounted on said first track for movement thereon. said first patient bed being oriented on said first transportable table for facilitating transfer of said first patient bed with a patient thereon from said first transportable table onto said patient bed support, and from said patient bed support back onto said first transportable table; and
    automating both movement of said first transportable table between said scanner room and said first patient room, and transfer of said first patient bed between said patient bed support and said first transportable table.

16. The method of claim 15, further comprising:
    installing a first track between another side of said patient bed support and a point in a second patient room, said another side being opposite said one side of said patient bed support;
    removably attaching a second patient bed to the top of a second transportable table mounted on said second tract for movement thereon, said second patient bed being oriented on said second transportable table for facilitating transfer of said second patient bed from said second transportable table onto said patient bed support, and from said patient bed support back onto said second transportable table.

17. A patient handling apparatus for use in conjunction with a patient scanning system, comprising:
    a transportable table having means for removably attaching a patient bed thereto;
    transfer means for selectively directing movement of the transportable table so as to carry said patient bed from a staging room to a position in a scanner room immediately juxtaposed to a patient bed support in said scanner room, said transfer means including means for automating the movement and transfer of said patient bed to and from said scanner room and said staging room.

18. The apparatus of claim 17 wherein said transfer means including a track upon which the transportable table travels.

19. The apparatus of claim 17 wherein said transfer means further comprises a processor programmed for controlling the movement of the transportable table.

20. The apparatus of claim 17 wherein said transfer means includes a track upon which the transportable table travels and wherein the processor controls the movement of the transportable table along the track.

* * * * *